United States Patent [19]

Samain

[11] Patent Number: 5,715,845

[45] Date of Patent: Feb. 10, 1998

[54] PROCESS FOR THE PERMANENT RESHAPING OF KERATINOUS MATERIAL

[75] Inventor: Henri Samain, Bievres, France

[73] Assignee: L'Oreal, Paris, France

[21] Appl. No.: 561,695

[22] Filed: Nov. 22, 1995

[30] Foreign Application Priority Data

Nov. 24, 1994 [FR] France ................... 94 14109

[51] Int. Cl.$^6$ ..................................... A45D 7/04
[52] U.S. Cl. ................ 132/204; 132/202; 132/203; 132/205; 132/209
[58] Field of Search ................... 132/204, 202, 132/203, 205, 208, 209; 424/70.2, 71, 72; 8/127; 514/544

[56] References Cited

U.S. PATENT DOCUMENTS

| | | |
|---|---|---|
| 2,540,980 | 2/1951 | Den Beste et al. |
| 3,973,574 | 8/1976 | Minagawa et al. |
| 4,532,950 | 8/1985 | Lang et al. ............... 132/204 |
| 5,061,483 | 10/1991 | Tieckelmann ............ 424/72 |
| 5,100,436 | 3/1992 | Wenke. |
| 5,178,637 | 1/1993 | Lagrange et al. |
| 5,184,630 | 2/1993 | Jung ....................... 132/202 |
| 5,225,191 | 7/1993 | De Labbey ............... 424/71 |
| 5,277,206 | 1/1994 | Rose et al. ............... 132/204 |
| 5,419,895 | 5/1995 | Kubo et al. .............. 132/204 |
| 5,441,729 | 8/1995 | Salce et al. .............. 132/204 |
| 5,456,907 | 10/1995 | Nandagiri et al. ........ 132/204 |

FOREIGN PATENT DOCUMENTS

| | | |
|---|---|---|
| 022996 | 1/1981 | European Pat. Off. . |
| 0328816 | 8/1989 | European Pat. Off. . |
| 0369356 | 5/1990 | European Pat. Off. . |
| 0462857 | 12/1991 | European Pat. Off. . |
| 479297 | 10/1969 | Switzerland . |
| WO 94/00099 | 1/1994 | WIPO . |

OTHER PUBLICATIONS

Patent Abstracts of Japan, vol. 14, No. 265 (C–726), "Agent for Preventing Hair Damage", Patent Date: Mar. 19, 1990.

*Primary Examiner*—Gene Mancene
*Assistant Examiner*—Pedro Philogene
*Attorney, Agent, or Firm*—Finnegan, Henderson, Farabow, Garrett & Dunner, L.L.P.

[57] ABSTRACT

A treatment process for the permanent reshaping of keratinous material, of the type comprising a reduction phase and an oxidation phase, the reduction phase being performed by application onto the keratinous material to be treated of a reducing composition containing at least one thiol, the keratinous material being impregnated with at least one manganese salt prior to/or during the reduction step, the process being characterized in that the keratinous material is treated, during or after the reduction phase and before the oxidation phase, in the presence of at least one agent which neutralizes the activity of the manganese salt in oxidation dyeing processes.

22 Claims, No Drawings

PROCESS FOR THE PERMANENT RESHAPING OF KERATINOUS MATERIAL

The present invention is directed to a novel process for the treatment of keratinous material, in particular human keratinous fibres such as the hair, for the purpose of obtaining a permanent reshaping of these fibres, in particular in the form of permanent-waved hair; it being possible in particular for the process to be used in the field of professional hair salons, beauty salons, cosmetic salons and the like.

It is known that the most common technique for obtaining a permanent reshaping of the hair consists, in a first stage, in opening the -S-S- disulphide bridges of keratin (cystine) using a composition containing a reducing agent (reduction step) and, preferably after having rinsed the hair thus treated, in then reforming the disulphide bridges, in a second stage, by applying, to the hair which has been placed under tension beforehand, by curlers and the like, an oxidizing composition (oxidation step, also known as the fixing step) in order to finally give the hair the desired shape. This technique thus makes it possible without distinction to make the hair wavy or to straighten it or remove the curliness therefrom. The new shape in which the hair is set by a chemical treatment such as that above is remarkably long-lasting and particularly resists the action of washing with water or shampoo. This is in contrast to the simple standard techniques for the temporary reshaping of hair, such as hair setting.

The reducing compositions which may be used to carry out the first step of a permanent-waving operation generally contain, as reducing agents, sulphites, bisulphites or thiols. Among the latter agents there may be mentioned cysteine and various derivatives thereof, cysteamine and derivatives thereof, thiolactic acid, thioglycolic acid and esters thereof, in particular glyceryl monothioglycolate, and thioglyceryol.

In order to perform the above-mentioned fixing step, use is usually made, in practice, of compositions based on aqueous hydrogen peroxide solutions or on alkali metal bromates.

It is known from the state of the art to perform processes for the permanent reshaping of the hair in the presence of manganese salts.

U.S. Pat. No. 2,540,980, the disclosure of which is specifically incorporated herein by reference, describes treatment of the hair with a manganese salt in a permanent-reshaping process. The manganese salt acts as an oxidation catalyst with atmospheric oxygen. This process makes it possible to dispense with a fixing step requiring the use of a fixing agent of the aqueous hydrogen peroxide solution type. The treatment consists either of a pretreatment of the hair with the manganese salt before application of the reducing composition, or of application of a reducing composition containing a manganese salt.

French patent FR-A-1,505,992, the disclosure of which is specifically incorporated herein by reference, describes a process for the pretreatment of hair which is subsequently to undergo setting, the process consisting of a chemical process similar to that of a permanent-waving operation but without subjecting the hair to a mechanical reshaping, i.e., the absence of curlers or rollers. The settings performed on hair thus treated are of better quality and better hold. The fixing step of the process may be performed in the absence of an oxidizing agent, such as aqueous hydrogen peroxide solution, by adding manganese salts to the reducing composition; the effect of these is to catalyse the oxidation in the presence of atmospheric oxygen. According to Examples 4 and 6 of FR-A-1,505,992, a catalytic lotion containing manganese salts may be applied after the rinsing operation following the reduction step, for the purpose of neutralizing the keratin. The application of such a lotion makes it possible to remove any odor originating from the mercaptan employed during the reduction phase.

The Inventor has observed that the presence, even the residual presence, of manganese salts on the hair causes problems regarding the ability which the hair has to then be dyed properly. Thus, it has been observed for oxidation dyes applied to hair thus treated that the dyeing results are different from those obtained on permanent-waved hair with no supply of manganese salts: the shades are different. The hairstylist will therefore not obtain the result usually obtained with untreated hair. This also poses a problem in all the cases where the dyeing operation is performed on a head of hair which has been permanent-waved but which has, in the meantime, also grown longer: a difference in coloration is then observed between the permanent-waved hair and the non-permanent-waved new growth of hair.

The aim of the present invention is to solve the above problems and to provide a treatment process which makes it possible to obtain a uniform coloration when it is applied to hair which has previously been permanent-waved by a process employing manganese salts.

Thus, after considerable research conducted in this matter, the Inventor has found that the use of agents which neutralize the activity of the manganese salts, before the oxidation step of a permanent reshaping process, makes it possible to successfully overcome the various drawbacks which are inherently associated with the application of manganese salts on the hair during permanent-waving operations.

A subject of the present invention is thus a novel treatment process for the permanent reshaping of keratinous material, in particular the hair, of the type comprising a reduction phase and an oxidation phase, the reduction phase comprising application onto the keratinous material to be treated of a reducing composition containing at least one thiol, the keratinous material being impregnated with at least one manganese salt prior to or during the reduction step, the process also being characterized in that the keratinous material is treated, during or after the reduction phase and before the oxidation phase, by contact with at least one agent which neutralizes the activity of the manganese salt.

The process according to the invention has the advantage of being able to retain the deodorizing effect of the manganese salts during the reduction phase of the permanent-waving operation.

Although the account which follows essentially focuses on the particular case of the treatment of the hair, it will be noted here that the process according to the invention may be applied to any keratinous material in general, in particular eyelashes, moustaches, body hairs, wools and the like.

According to the invention, the keratinous material is impregnated with at least one manganese salt before or during the reduction phase. This impregnation may be performed in several ways. The manganese salt may be present in the reducing composition, or may be applied to the keratinous material from a separate composition at the same time as the reducing composition.

In another variant, a so-called "prelotion" composition containing at least one manganese salt is applied to the keratinous material before the application of the reducing composition. It is equally possible for the reducing composition to contain at least one manganese salt. The head of hair on which the prelotion has been applied is preferably allowed to stand for a period ranging from 10 seconds to 30 minutes, and more preferably for a period ranging from 1 to 5 minutes.

The manganese salts which may be used within the context of the present invention preferably have a manganese oxidation level equal to or greater than 2. Examples of manganese which may be mentioned are manganese (II), manganese (III), manganese (IV), manganese (V) and manganese (VII).

Among the manganese salts which may more preferably be used, there may be mentioned manganese diacetate and hydrates thereof such as, for example, manganese diacetate tetrahydrate, manganese dichloride and hydrates thereof; manganese sulphates; manganese carbonates; manganese dihydrogen carbonates; manganese acetylacetonate; manganese triacetate and hydrates thereof; and manganese tetrachloride.

In the case where the manganese salt is present in the reducing composition, the content of this salt, expressed as manganese equivalents, preferably ranges from 0.4 mg to 20 mg per 100 g of reducing composition, and more preferably from 0.8 mg to 10 mg per 100 g of reducing composition.

The prelotion may be of the rinsed type, that is to say that after application of the prelotion and after being optionally allowed to stand, the keratinous material thus treated is rinsed and the reducing composition is then applied.

The prelotion may also be of the leave-in type, that is to say that after application of the prelotion and after being optionally allowed to stand, the keratinous material is not rinsed, and the reducing composition is applied.

In the case of a prelotion of the rinsed type, the concentration of manganese salt, expressed as manganese equivalents, preferably ranges from 0.8 mg to 80 mg, and more preferably ranges from 1.6 mg to 64 mg, per 100 g of the prelotion.

In the case of a prelotion of the leave-in type, the concentration of manganese salt, expessed as manganese equivalents, preferably ranges from 0.6 mg to 40 mg, and more preferably ranges from 1.2 mg to 32 mg, per 100 g of the prelotion.

According to the invention, the thiol content in the reducing composition preferably ranges from 1 to 20% by weight relative to the total weight of the composition. The pH of the reducing composition preferably ranges from 5 to 10.

The expression agent which neutralizes the activity of the manganese salt is understood by those skilled in the art to denote and to cover in particular any constituent capable of inhibiting the activity of the manganese salt in oxidation dyeing processes.

By way of agent which neutralizes the activity of the manganese salt which may be used according to the invention, there may preferably be mentioned complexing agents having anionic and amine functions and zeolites.

The term complexing agent refers to a compound which is capable of chelating a manganese salt.

The anionic functions may preferably be carboxylic acid, phosphonic acid or sulphonic acid functions.

By way of complexing agents having carboxylic acid functions, there may preferably be mentioned ethylenediamine-tetraacetic acid and the pentasodium salt of diethylenetriaminepentaacetic acid.

By way of complexing agents having phosphonic acid functions, there may preferably be mentioned alkylenediamino-poly(methylenephosphonic) acids and salts thereof, and in particular ethylenediaminetetra (methylene-phosphonic) acid, sold under the name DEQUEST 2041 by the company Monsanto, as well as the pentasodium salt thereof (DEQUEST 2046), hexamethylenediaminetetra(methylene-phosphonic) acid (DEQUEST 2051) and the hexapotassium salt thereof (DEQUEST 2054), diethylenetriamine penta(methylenephosphonic) acid (DEQUEST 2060S) and the heptasodium salt thereof (DEQUEST 2066), and 1-hydroxyethylidene-1, 1-diphosphonic acid (DEQUEST 2010).

The term zeolites refers to any crystalline alkali metal aluminosilicate, preferably sodium aluminosilicate, of natural or synthetic origin.

According to the invention, the agent which neutralizes the activity of the manganese salt may preferably be applied in composition form at various moments in the process, that is to say, during or after the reduction phase and before the oxidation phase.

When the agent which neutralizes the activity of the manganese salt is applied after the reduction phase, it may preferably be applied before or after rinsing out of the reducing composition. In this case, when the agent which neutralizes the activity of the manganese salt is a complexing agent, this agent is present in the composition applied at a concentration which preferably ranges from 0.01% to 5% by weight relative to the total weight of the composition containing it. The composition is preferably allowed to act until the hair is impregnated therewith, that is to say, for example, for a period preferably ranging from 15 seconds to 15 minutes. The pH of the composition preferably ranges from 3 to 11, and more preferably ranges from 5 to 9.

When the agent which neutralizes the activity of the manganese salt is applied during the reduction phase, it is preferably present in the reducing composition. In this case, the concentration of the neutralizing agent is preferably controlled so as not to lose the deodorizing effect of the manganese salt. When the neutralizing agent is a complexing agent, it is preferably present in the reducing composition at a concentration such that the content of ligands in the complexing agent per manganese atom is preferably equal to or greater than 1 and equal to or less than 5, and more preferably equal to or greater than 2 and equal to or less than 4.

For the purpose of reinforcing the action of the complexing agent carrying anionic and amine functionality towards the activity of the manganese salt, this agent may be combined with other complexing agents containing no amine functions, such as (poly)carboxylic acids, among which there may be mentioned citric acid and carbonic acid.

The compositions used according to the invention may be, independently of each other, in the form of a lotion, which may or may not be thickened, a cream, a gel or any other suitable form. They may also preferably contain cosmetic adjuvants known in particular for their use in hair applications. The cosmetic adjuvant, for example, can be contained in the reducing composition, a composition containing at least one manganese salt, or a composition containing at least one agent which neutralizes the activity of the manganese salt.

If a reducing composition containing at least one manganese salt is used in the process according to the invention, it is preferably packaged in the form of a multi-compartment device or "kit", the first compartment preferably containing the thiol and the second compartment preferably containing the manganese salt, the other ingredients being completely or partly distributed in the compartment containing the thiol and/or in the compartment which includes the manganese salt. The two compartments are preferably mixed together at the time of use. It is also possible to use a single packaging containing the mixture in the absence of air (low volume of air, packaging without air uptake, packaging in aerosol form).

The oxidation phase of the process according to the invention may be performed by application of an oxidizing composition or, optionally, by allowing atmospheric oxygen to act.

The oxidizing composition is preferably of the type commonly used in hair treatment processes and contains, as oxidizing agent, aqueous hydrogen peroxide solution, an alkali metal bromate, a persalt, a polythionate or a mixture of alkali metal bromate and persalt. The concentration of aqueous hydrogen peroxide solution preferably ranges from 1 to 20 volumes and more preferably ranges from 1 to 10 volumes. The concentration of alkaki metal bromate preferably ranges from 2 to 12% and that of persalt preferably ranges from 0.1 to 15% by weight relative to the total weight of the oxidizing composition. The pH of the oxidizing composition preferably ranges from 2 to 10. This oxidation may be carried out immediately or may be delayed.

Another subject of the invention is a composition comprising a thiol, a manganese salt and an agent which neutralizes the activity of the manganese salt.

The agent which neutralizes the activity of the manganese salt is chosen from the complexing agents containing anionic and amine functions and the zeolites as defined above.

In particular, when the neutralizing agent is a complexing agent containing anionic and amine functions, its concentration is preferably such that the content of ligands in the complexing agent per manganese atom is equal to or greater than 1 and equal to or less than 5, and more preferably equal to or greater than 2 and equal to or less than 4.

Another subject of the invention is the use of this composition as a reducing composition in a process for the permanent reshaping of keratinous material.

Concrete examples illustrating the invention will now be given.

EXAMPLE A

Five reducing compositions which had the following characteristics were prepared:

Reducing Composition No. 1 (comparative):

| | |
|---|---|
| thioglycolic acid | 9.2 g |
| sodium carbonate | 1 g |
| monoethanolamine qs | pH 8.5 |
| cocoylamidopropylbetaine/ glyceryl monolaurate mixture (25/5), sold under the name "TEGOBETAINE HS" by the company Goldschmidt at a concentration of 30% active material | 0.3 g AM |
| demineralized water qs | 100 g |

The composition was introduced into an aerosol can in the presence of 10 g of butane.

Reducing Composition No. 2 (comparative):

| | |
|---|---|
| thioglycolic acid | 9.2 g |
| sodium carbonate | 1 g |
| monoethanolamine qs | pH 8.5 |
| manganese acetate tetrahydrate | 0.01 g (22 µg per g) |
| cocoylamidopropylbetaine/ glyceryl monolaurate mixture (25/5), sold under the name "TEGOBETAINE HS" by the company Goldschmidt at a concentration of 30% active material | 0.3 g AM |
| demineralized water qs | 100 g |

The manganese salt was added at the last moment.

The composition was introduced into an aerosol can in the presence of 10 g of butane.

Reducing Composition No. 3 (invention):

| | |
|---|---|
| thioglycolic acid | 9.2 g |
| sodium carbonate | 1 g |
| monoethanolamine qs | pH 8.5 |
| manganese acetate tetrahydrate | 0.01 g (22 µg per g) |
| cocoylamidopropylbetaine/ glyceryl monolaurate mixture (25/5), sold under the name "TEGOBETAINE HS" by the company Goldschmidt at a concentration of 30% active material | 0.3 g AM |
| diethylenetriamine-pentaacetic acid trihydrate containing 40% active material | 0.04 g (3.3 ligands per manganese atom) |
| demineralized water qs | 100 g |

The manganese salt was added at the last moment.

The composition was introduced into an aerosol can in the presence of 10 g of butane.

Reducing Composition No. 4 (comparative):

| | |
|---|---|
| thioglycolic acid | 9.2 g |
| sodium carbonate | 1 g |
| monoethanolamine qs | pH 8.5 |
| manganese acetate tetrahydrate | 0.01 g (22 µg per g) |
| cocoylamidopropylbetaine/ glyceryl monolaurate mixture (25/5), sold under the name "TEGOBETAINE HS" by the company Goldschmidt at a concentration of 30% active material | 0.3 g AM |
| o-phenanthroline monohydrate | 0.012 g (3.3 ligands per manganese atom) |
| demineralized water qs | 100 g |

O-Phenanthroline is a complexing agent carrying amine functionality.

The manganese salt was added at the last moment.

The composition was introduced into an aerosol can in the presence of 10 g of butane.

Reducing Composition No. 5 (comparative):

| | |
|---|---|
| thioglycolic acid | 9.2 g |
| sodium carbonate | 1 g |
| monoethanolamine qs | pH 8.5 |
| manganese acetate tetrahydrate | 0.01 g (22 µg per g) |
| cocoylamidopropylbetaine/ glyceryl monolaurate mixture (25/5), sold under the name "TEGOBETAINE HS" by the company Goldschmidt at a concentration of 30% active material | 0.3 g AM |
| diethylenetriamine-pentaacetic acid trihydrate containing 40% active material | 0.10 g (8 ligands per manganese atom) |
| demineralized water qs | 100 g |

The manganese salt was added at the last moment.

The composition was introduced into an aerosol can in the presence of 10 g of butane.

A permanent-waving operation was carried out on wigs consisting of 15 g of European grey hair containing 70% white hairs, using each of the reducing compositions, according to the following procedure: the reducing composition was applied to the wet, wound hair (diameter of the rollers: 9 mm), a plastic hood was then placed over the head of hair and left in place for 15 minutes. The hood was then removed and the odor released by the wigs was evaluated by a panel of 12 people. The hair was next rinsed and an oxidizing composition having the following characteristics was then applied:

| | |
|---|---|
| aqueous hydrogen qs peroxide solution | 8 V |
| citric acid qs | pH 3 |
| demineralized water qs | 100 g |

The composition was allowed to act for 10 minutes. The rollers were removed and the hair was then rinsed with water and finally dried.

The odor released by the wigs was rated from 0 to 5, a rating of 0 being attributed when the odor smelled very unpleasant and a rating of 5 corresponding to no detected odor.

The results obtained were as follows:

| Wig No. | Reducing composition | Odor perceived |
|---|---|---|
| 1 | 1 | 1 |
| 2 | 2 | 3.4 |
| 3 | 3 | 3.2 |
| 4 | 4 | 3.2 |
| 5 | 5 | 1.5 |

A dye composition which had the following characteristics was then applied to each wig No. 1 to 4:
Dye Composition:

| | |
|---|---|
| para-phenylenediamine | 0.4 g |
| para-aminophenol | 0.24 g |
| 1-methyl-2-hydroxy-4-β-hydroxyethylaminobenzene | 1.2 g |
| nonylphenol polyoxyethylenated with 9 mol of ethylene oxide | 3 g |
| oleyl alcohol | 18 g |
| ethyl alcohol | 9 g |
| benzyl alcohol | 11 g |
| ethylenediaminetetraacetic acid | 0.2 g |
| aqueous ammonia at 220° Be | 12.9 g |
| monoethanolamine | 6.5 g |
| ammonium thiolactate containing 50% active material | 0.8 g |
| 1-phenyl-3-methyl-5-pyrazolone | 0.15 g |
| demineralized water qs | 100 g |

At the time of use, this composition was mixed weight for weight with a 20-volume aqueous hydrogen peroxide solution.

The dye composition was allowed to act for 30 minutes and the hair was then washed using a shampoo, and dried.

The colors obtained for each wig were evaluated by measuring the L, a and b trichromatic coordinates of the hair (Minolta CHROMA METER 2002 colorimeter).

The following results were obtained:

| Wig | Coloration | | |
|---|---|---|---|
| | L | a | b |
| 1 | 29.5 | 16 | 11.3 |
| 2 | 28.8 | 12.8 | 8.3 |

-continued

| Wig | Coloration | | |
|---|---|---|---|
| | L | a | b |
| 3 | 29 | 14.3 | 9.6 |
| 4 | 28.8 | 12.9 | 8.5 |

It was observed that the use of a composition free of complexing agent on wig No. 2 caused a change in the color relative to the coloration obtained on wig No. 1: the decrease in the parameters a and b reflects a different shade. This indeed demonstrated that the use of manganese salts during the reduction phase makes it possible to decrease the odor released by the hair (rating equal to 3.4) but poses a problem with regard to the dyeing results.

When the reduction phase was performed in the presence of a complexing agent containing anionic functionality and amine functionality, and in compliance with a ligand/manganese ratio<5 (Example 3), it was observed that the odor released by the hair was reduced and that when the dyeing was carried out after the permanent-waving operation, the change in the color was also reduced (parameters a and b of wig No. 3 were higher than those of wig No. 2). If a complexing agent was used which had only amine functions (free of anionic functions) (Example 4), it was observed that the odor released by the hair was reduced but the change in the color remained large (parameters a and b of wig No. 4 were close to those of wig No. 2). Finally, if a complexing agent containing anionic functionality and amine functionality was used, with a ligand/manganese ratio>5 (Example 5), no action was observed with regard to the odor released by the hair (rating equal to 1.5): there was no deodorizing effect.

Thus, wig No. 3 had the best deodorizing and dyeing results.

EXAMPLE B

The procedure was performed as in Example A on two wigs (No. 6 and No. 7), using the reducing compositions No. 1 and No. 3 respectively, except that a so-called semi-permanent lotion which had the characteristics below was applied to wig No. 7 after evaluation of the odor released by the wigs and before rinsing of the reducing composition:
Semi-permanent lotion:

| | |
|---|---|
| diethylenetriaminepentaacetic acid trihydrate as an aqueous solution containing 40% active material | 2 g |
| hydrochloric acid qs | pH 5.5 |
| demineralized water qs | 100 g |

The following results were obtained:

| Wig No. | Reducing Composition | Semi-permanent Lotion | Odor | Coloration | | |
|---|---|---|---|---|---|---|
| | | | | L | a | b |
| 6 | 1 | No | 1 | 29.5 | 16 | 11.3 |
| 7 | 3 | Yes | 3.2 | 29.5 | 15.8 | 11.1 |

The result of the olfactory test shows that wig No. 7 smelled very little on removal of the hood. Furthermore, wig No. 7 had a dyeing result which was comparable to that usually obtained after permanent-waving operations carried out without manganese salt.

EXAMPLE C

The process was performed as in Example B on wig No. 8, using reducing composition No. 2. The semi-permanent lotion was applied after reduction and before fixing.

The process was performed as in Example A on wig No. 9, using reducing composition No. 2, except that the semi-permanent lotion of Example B was applied before rinsing out the oxidizing composition.

The following results were obtained:

| Wig No. | Reducing Composition | Semi-permanent Lotion | Odor | Coloration L | a | b |
|---|---|---|---|---|---|---|
| 1 | 1 | No | 1 | 29.5 | 16.0 | 11.1 |
| 8 | 2 | after reduction | 3.3 | 29.3 | 15.1 | 11.0 |
| 9 | 2 | after fixing | 3.3 | 29.0 | 12.4 | 8.4 |

The result of the olfactory test shows that wigs Nos. 8 and 9 smelled very little on removal of the hood. When the dyeing was carried out after the permanent-waving operation, there was a large color change for wig No. 9 (parameters a and b of wig No. 9 were smaller than those of wig No. 1), whereas it remained unchanged for wig No. 8 (parameters a and b of wig No. 8 were close to those of wig No. 1). Thus, the application of a lotion with a complexing agent containing anionic functionality and amine functionality after the fixing step does not make it possible to solve the problem with regard to the dyeing results, whereas the application of the same lotion before the fixing step solved this problem.

What is claimed is:

1. A treatment process for the permanent reshaping of keratinous material, which comprises a reduction phase and an oxidation phase,
   wherein said reduction phase comprises application of reducing composition containing at least one thiol to said keratinous material,
   wherein said keratinous material is impregnated with at least one manganese salt prior to or during said reduction phase, and
   wherein said keratinous material is contacted, during or after said reduction phase and before said oxidation phase, with at least one agent which neutralizes the activity of the manganese salt wherein said at least one agent is a zeolite or a complexing agent containing anionic and amine functions.

2. A process according to claim 1, wherein said at least one agent which neutralizes the activity of the manganese salt is selected from complexing agents containing anionic and amine functions and wherein said complexing agent contains at least one ligand and is present in said reducing composition at a concentration such that the content of said ligand in said complexing agent per manganese atom is equal to or greater than 1 and equal to or less than 5.

3. A process according to claim 2, wherein said anionic functions are carboxylic acid, phosphonic acid or sulphonic acid functions.

4. A process according to claim 2, wherein said complexing agent is ethylenediaminetetraacetic acid or the pentasodium salt of diethylenetriaminepentaacetic acid.

5. A process according to claim 2, wherein said complexing agent is an alkylenediaminopoly(methylenephosphonic) acid selected from ethylenediaminetetra(methylenephosphonic) acid, hexamethylenediaminetetra-(methylenephosphonic) or diethylenetriamiepenta (methylenephosphonic) acid and a salt of any of said acids.

6. A process according to claim 1, wherein said at least one agent which neutralizes the activity of the manganese salt is a zeolite.

7. A process according to claim 1, wherein said at least one agent which neutralizes the activity of the manganese salt is applied to said keratinous material in the form of a composition and is applied before or after said reducing composition is rinsed out of said keratinous material.

8. A process according to claim 7, wherein said at least one agent which neutralizes the activity of the manganese salt is selected from complexing agents containing anionic functions and amine functions and is present at a concentration which ranges from 0.01% to 5% by weight relative to the total weight of the composition, and further wherein said complexing agent contains at least one ligand and is present at a concentration such that the content of said ligand in said complexing agent per manganese atom is equal to or greater than 1 and equal to or less than 5.

9. A process according to claim 7, wherein said composition containing said at least one agent which neutralizes the activity of the manganese salt is allowed to act for a period of time which ranges from 15 seconds to 15 minutes.

10. A process according to claim 7, wherein said composition containing said at least one agent which neutralizes the activity of the manganese salt has a pH which ranges from 3 to 11.

11. A process according to claim 10, wherein the pH of said composition containing said at least one agent which neutralizes the activity of the manganese salt ranges from 5 to 9.

12. A process according to claim 1, wherein said reducing composition contains said at least one agent which neutralizes the activity of the manganese salt.

13. A process according to claim 2, wherein the content of said ligand in said complexing agent per manganese atom is equal to or greater than 2 and equal to or less than 4.

14. A process according to claim 1, further comprising at least one cosmetic adjuvant.

15. A process according to claim 1, wherein said keratinous material comprises hair.

16. A composition, which comprises a thiol, at least one manganese salt and at least one agent which neutralizes the activity of the manganese salt.

17. A composition according to claim 16, wherein said agent which neutralizes the activity of the manganese salt is selected from complexing agents containing anionic and amine functions and wherein said complexing agent contains at least one ligand and is present at a concentration such that the content of said ligand in the complexing agent per manganese atom is equal to or greater than 1 and equal to or less than 5.

18. A composition according to claim 17, wherein said anionic functions are carboxylic acid, phosphonic acid or sulphonic acid functions.

19. A composition according to claim 17, wherein said complexing agent is ethylenediaminetetraacetic acid or the pentasodium salt of diethylenetriaminepentaacetic acid.

20. A composition according to claim 17, wherein said complexing agent is an alkylenediaminopoly (methylenephosphonic) acid selected from ethylenediaminetetra(methylenephosphonic) acid, hexamethylenediaminetetra-(methylenephosphonic) and diethylenetriamiepenta(methylenephosphonic) acid or a salt of any of said acids.

21. A composition according to claim 16, wherein said agent which neutralizes the activity of the manganese salt is a zeolite.

22. A treatment process for the permanent reshaping of keratinous material which comprises application to said keratinous material of a reducing composition which comprises a thiol, at least one manganese salt and at least one agent which neutralizes the activity of the manganese salt.

* * * * *

UNITED STATES PATENT AND TRADEMARK OFFICE
CERTIFICATE OF CORRECTION

PATENT NO. : 5,715,845
DATED : February 10, 1998
INVENTOR(S) : SAMAIN

It is certified that error appears in the above-indentified patent and that said Letters Patent is hereby corrected as shown below:

In Claim 5, Col. 10, line 3, "diethylenetriamiepenta" should read --diethylenetriaminepenta--.

In Claim 20, Col. 10, line 66, "diethylenetriamiepenta" should read --diethylenetriaminepenta--.

Signed and Sealed this

Fifth Day of May, 1998

Attest:

BRUCE LEHMAN

*Attesting Officer*   *Commissioner of Patents and Trademarks*